(12) United States Patent
Dumas, III et al.

(10) Patent No.: US 9,707,341 B2
(45) Date of Patent: Jul. 18, 2017

(54) INFUSION SYSTEM AND METHOD OF USE WHICH PREVENTS OVER-SATURATION OF AN ANALOG-TO-DIGITAL CONVERTER

(71) Applicant: ICU Medical, Inc., San Clemente, CA (US)

(72) Inventors: John Hicks Dumas, III, Libertyville, IL (US); Paul T. Kotnik, Commerce Township, MI (US); Kunal Sur, Evanston, IL (US); Anatoly S. Belkin, Glenview, IL (US); Timothy L. Ruchti, Gurnee, IL (US)

(73) Assignee: ICU Medical, Inc., San Clemente, CA (US)

( * ) Notice: Subject to any disclaimer, the term of this patent is extended or adjusted under 35 U.S.C. 154(b) by 467 days.

(21) Appl. No.: 14/289,796

(22) Filed: May 29, 2014

(65) Prior Publication Data

US 2014/0358081 A1 Dec. 4, 2014

Related U.S. Application Data

(60) Provisional application No. 61/828,408, filed on May 29, 2013.

(51) Int. Cl.
*G01R 23/00* (2006.01)
*G01N 29/00* (2006.01)
(Continued)

(52) U.S. Cl.
CPC ........ *A61M 5/16831* (2013.01); *A61M 5/142* (2013.01); *A61M 5/365* (2013.01);
(Continued)

(58) Field of Classification Search
CPC .... A61M 5/36; A61M 5/365; A61M 5/16831; A61M 5/14232; A61M 2005/14208; A61M 2005/16868; A61M 2005/16872
(Continued)

(56) References Cited

U.S. PATENT DOCUMENTS 4,607,520 A 8/1986 Dam
5,455,423 A 10/1995 Mount et al.
(Continued)

FOREIGN PATENT DOCUMENTS

WO 96/41156 A1 12/1996
WO 98/44320 A1 10/1998
(Continued)

*Primary Examiner* — An Do
(74) *Attorney, Agent, or Firm* — Knobbe Martens Olson & Bear, LLP (57) ABSTRACT

To detect air in a fluid delivery line of an infusion system, infusion fluid is pumped through a fluid delivery line adjacent to at least one sensor. A signal is transmitted and received using the at least one sensor into and from the fluid delivery line. The at least one sensor is operated, using at least one processor, at a modified frequency which is different than a resonant frequency of the at least one sensor to reduce an amplitude of an output of the signal transmitted from the at least one sensor to a level which is lower than a saturation level of the analog-to-digital converter to avoid over-saturating the analog-to-digital converter. The signal received by the at least one sensor is converted from analog to digital using an analog-to-digital converter. The at least one processor determines whether air is in the fluid delivery line based on the converted digital signal.

20 Claims, 7 Drawing Sheets

(51) Int. Cl.
| | |
|---|---|
| *G01N 33/18* | (2006.01) |
| *A61M 5/168* | (2006.01) |
| *A61M 5/142* | (2006.01) |
| *A61M 5/36* | (2006.01) |
| *G01N 29/02* | (2006.01) |
| *G01N 29/34* | (2006.01) |
| *G01N 29/42* | (2006.01) |
| *H03M 1/12* | (2006.01) |

(52) U.S. Cl.
CPC ........... *G01N 29/02* (2013.01); *G01N 29/348* (2013.01); *G01N 29/42* (2013.01); *H03M 1/129* (2013.01); *A61M 2205/3306* (2013.01); *A61M 2205/3327* (2013.01); *A61M 2205/3375* (2013.01); *A61M 2205/52* (2013.01); *A61M 2205/702* (2013.01); *G01N 2291/014* (2013.01); *G01N 2291/02433* (2013.01)

(58) Field of Classification Search
USPC ............ 702/57, 56, 75, 104; 73/19.03, 19.1; 604/67, 500
See application file for complete search history.

(56) References Cited

U.S. PATENT DOCUMENTS

| | | | |
|---|---|---|---|
| 5,469,851 A | 11/1995 | Lipschutz | |
| 5,533,389 A | 7/1996 | Kamen et al. | |
| 5,590,653 A | 1/1997 | Aida et al. | |
| 5,993,393 A | 11/1999 | Ryan et al. | |
| 6,023,977 A | 2/2000 | Langdon et al. | |
| 6,212,936 B1 | 4/2001 | Meisberger | |
| 6,267,725 B1 | 7/2001 | Dubberstein et al. | |
| 6,516,667 B1 | 2/2003 | Broad et al. | |
| 6,978,779 B2 | 12/2005 | Haveri et al. | |
| 7,678,048 B1 | 3/2010 | Urbano et al. | |
| 7,786,909 B2 | 8/2010 | Udupa et al. | |
| 8,539,812 B2 * | 9/2013 | Stringham | G01N 29/032 73/1.82 |
| 8,821,432 B2 * | 9/2014 | Unverdorben | A61M 5/365 417/282 |
| 2005/0192529 A1 | 9/2005 | Butterfield et al. | |
| 2007/0084288 A1 | 4/2007 | Thomas | |
| 2009/0178485 A1 | 7/2009 | Thomas | |
| 2009/0223294 A1 | 9/2009 | Thomas | |
| 2010/0147081 A1 | 6/2010 | Thomas | |
| 2010/0212407 A1 | 8/2010 | Stringham et al. | |
| 2013/0345658 A1 * | 12/2013 | Browne | A61M 5/16831 604/500 |

FOREIGN PATENT DOCUMENTS

| | | |
|---|---|---|
| WO | 00/41621 A1 | 7/2000 |
| WO | 2011/017778 A1 | 2/2011 |

\* cited by examiner

INFUSION SYSTEM AND METHOD OF USE WHICH PREVENTS OVER-SATURATION OF AN ANALOG-TO-DIGITAL CONVERTER

FIELD OF THE DISCLOSURE

This disclosure relates to an infusion system and method of use which prevents over-saturation of an analog-to-digital converter being used to determine whether air is present in the infusion system.

BACKGROUND

The Symbiq™ infusion system, made by Hospira, Inc., previously detected whether air was present in the infusion system by operating one or more sensors at their resonant frequency, which was determined and set during calibration. The one or more sensors were used to transmit and receive a signal through a fluid delivery line of the infusion system in order to determine, based on the strength of the signal that propagated through the fluid delivery line, whether air, fluid, or some combination thereof was disposed in the fluid delivery line. Signals propagate better through liquid fluid than through air. The resonant frequency of the one or more sensors is the frequency at which the output of the signal transmitted from the one or more sensors is maximized for a given transfer medium such as for the infusion fluid contained within the fluid delivery line of the infusion system. Thus, conventional wisdom suggested that the one or more sensors would be most effective at their resonant frequency. However, analog-to-digital converters are used to convert the received analog signal from analog to digital in order for a processor to determine, based on the converted digital signal, whether air, fluid, or some combination thereof is disposed in the fluid delivery line of the infusion system. It has been observed or discovered by the Applicants that under certain conditions, analog-to-digital converters can become over-saturated if the output of the signal transmitted from the one or more sensors is too high.

A system and method is needed to overcome one or more issues of one or more of the existing systems and methods for detecting air in an infusion system.

SUMMARY

In one embodiment, an infusion system is disclosed for being operatively connected to a fluid delivery line and to an infusion container containing an infusion fluid. The infusion system includes a pump, at least one sensor, an analog-to-digital converter, at least one processor, and a memory. The at least one sensor is disposed adjacent to the fluid delivery line and configured to transmit and receive a signal to detect whether there is air in the fluid delivery line. The analog-to-digital converter is electronically connected to the at least one sensor for converting the received signal from analog to digital. The at least one processor is in electronic communication with the pump, the at least one sensor, and the analog-to-digital converter. The memory is in electronic communication with the at least one processor. The memory includes programming code for execution by the at least one processor. The programming code is configured to operate the at least one sensor at a modified frequency which is different than a resonant frequency of the at least one sensor in order to reduce an amplitude of an output of the signal transmitted from the at least one sensor to a level which is lower than a saturation level of the analog-to-digital converter.

In another embodiment, a method is disclosed for detecting air in a fluid delivery line of an infusion system. In one step, infusion fluid is pumped through a fluid delivery line adjacent to at least one sensor. In another step, a signal is transmitted and received using the at least one sensor into and from the fluid delivery line. The at least one sensor is operated, using at least one processor, at a modified frequency which is different than a resonant frequency of the at least one sensor in order to reduce an amplitude of an output of the signal transmitted from the at least one sensor to a level which is lower than a saturation level of an analog-to-digital converter to avoid over-saturating the analog-to-digital converter. In an additional step, the signal received by the at least one sensor is converted from analog to digital using the analog-to-digital converter.

In still another embodiment, a method is disclosed for arranging and using an infusion system. In one step, a resonant frequency of at least one sensor is determined. In another step, a saturation level of an analog-to-digital converter is determined. In still another step, the at least one sensor is disposed adjacent to a fluid delivery line. In yet another step, a pump is connected to the fluid delivery line. In another step, the analog-to-digital converter is electronically connected to the at least one sensor. In an additional step, at least one processor is electronically connected to the pump, to the at least one sensor, and to the analog-to-digital converter. In still another step, the at least one processor is programmed to operate the at least one sensor at a modified frequency which is different than the resonant frequency of the at least one sensor in order to reduce an amplitude of an output of a signal transmitted from the at least one sensor to a level which is lower than the saturation level of the analog-to-digital converter to avoid over-saturating the analog-to-digital converter.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

Applicants have discovered through testing of the Symbiq™ infusion system that when some sensors are operated at their resonant frequency the signal transmitted from the one or more sensors sometimes is over-saturated and causes the analog-to-digital converter to become over-saturated. Variation in sensor manufacturing and assembly, especially bonding of the piezo-electric element to the supporting body in an ultrasonic sensor, can be significant. Some piezo-electric elements may be extremely well bonded within the sensor assembly while others may have many gaps, voids or air bubbles in the bonding of the element to the sensor body. Sensors with few bonding imperfections may have high output amplitude, particularly at resonant frequency. Applicants have further discovered that this high amplitude, over-saturated signal sometimes reduces the accuracy and reliability of the analog-to-digital converters which may not correctly convert the received over-saturated signal. Applicants have additionally discovered that this could lead to errors in the infusion system's determination as to whether or not air is contained in the infusion system and the generation of alarms.

Figure 1:
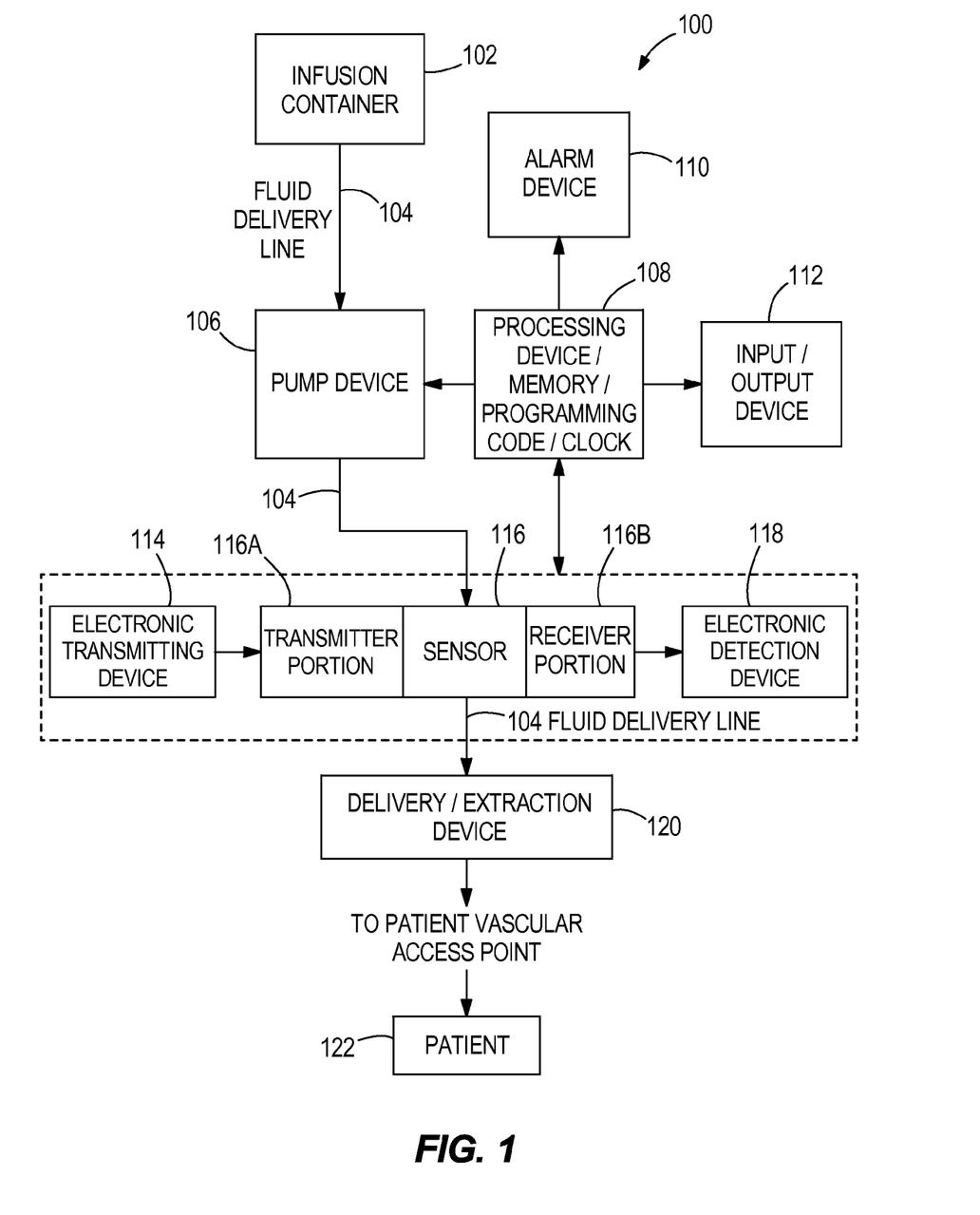
FIG. 1 illustrates a block diagram of an infusion system under one embodiment of the disclosure.

FIG. 1 illustrates a block diagram of an infusion system 100 under one embodiment of the disclosure. The infusion system 100 comprises: an infusion container 102; a fluid delivery line 104; a pump device 106; a processing device 108; an alarm device 110 that generates an audio, visual, other sensory signal or the like to a user; an input/output device 112; an electronic transmitting device 114; a sensor 116; an electronic detection device 118; and a delivery/extraction device 120. The infusion system 100 may comprise the Plum A+™, Gemstar™, Symbiq™, or other type of infusion system. The infusion container 102 comprises a container for delivering fluid such as IV fluid or a drug to the patient 122. The fluid delivery line 104 comprises one or more tubes, connected between the infusion container 102, the pump device 106, the sensor 116, and the delivery/extraction device 120, for transporting fluid from the infusion container 102, through the pump device 106, through the sensor 116, through the delivery/extraction device 120 to the patient 122. The fluid delivery line 104 may also be used to transport blood, extracted from the patient 122 using the delivery/extraction device 120, through the sensor 116 as a result of a pumping action of the pump device 106. The pump device 106 comprises a pump for pumping fluid from the supply container 102 or for pumping blood from the patient 122. The pump device 106 may comprise a plunger based pump, a peristaltic pump, or another type of pump.

The processing device 108 comprises at least one processor for processing information received from the electronic detection device 118 and/or the sensor 116 and for executing one or more algorithms to determine if air, fluid, or some combination thereof is located in the fluid delivery line 104 at the location of the sensor 116. The processing device 108 is in electronic communication with the pump device 106, the electronic transmitting device 114, the sensor 116, the electronic detection device 118, the input/output device 112, and the alarm device 110. The processing device 108 includes or is in electronic communication with a computer readable memory, containing programming code containing the one or more algorithms for execution by the at least one processor, and a clock.

The alarm device 110 comprises an alarm, triggered by the processing device 108, for notifying the clinician (also referred to as 'user' herein) as to the presence of air being disposed in the fluid delivery line 104 at the location of the sensor 116. The alarm device 110 may be configured to stop the pump device 106 prior to an air embolism being delivered through the fluid delivery line 104 and the delivery/extraction device 120 to the patient 122.

The input/output device 112 comprises a device which allows a clinician to input or receive information. The input/output device 112 allows a clinician to input or receive information regarding the infusion. For instance, the clinician may use the input/output device 112 to input or select a medication infusion program to be applied by the processing device 108, to set settings for the processing device 108 to apply in using the programming code containing the algorithm(s), or to input other type of information. The input/output device 112 may further output information to the clinician. In other embodiments, any of the information inputted into the input/output device 112 may be pre-installed into the programming code or the processing device 108.

The delivery/extraction device 120 comprises a patient vascular access point device for delivering fluid from the infusion container 102 to the patient 122, or for extracting blood from the patient 122. The delivery/extraction device 120 may comprise a needle, a catheter, or another type of delivery/extraction device. In other embodiments, the infusion system 100 of FIG. 1 may be altered to vary the components, to take away one or more components, or to add one or more components.

The electronic transmitting device 114 comprises electronic circuitry, connected to the sensor 116, which transmits a signal from a transmitter portion 116A of the sensor 116, through the fluid delivery line 104, to a receiver portion 116B of the sensor 116. The transmitter portion 116A and the receiver portion 116B are disposed on opposed sides of the fluid delivery line 104. The receiver portion 116B of the sensor is electronically connected to the electronic detection device 118. The sensor 116 may comprise an air-in-line sensor for sensing, with the assistance of the electronic detection device 118 and the processing device 108, whether air, fluid, or some combination thereof is contained in the fluid delivery line 104. The sensor 116 is disposed adjacent to and/or connected to the fluid delivery line 104 distal of the pump device 106. In other embodiments, the sensor 116 may be located proximal to the pump device 106 or may be located in both proximal and distal positions.

The transmitter and receiver portions 116A and 116B of the sensor 116 sense the presence of air, fluid, or some combination thereof within the fluid delivery line 104. The transmitter and receiver portions 116A and 116B of the sensor 116 comprise a transducer such as an ultrasonic sensor, an acoustic sensor, an optical sensor, or another type of sensor. Alternate arrangements of the sensor transmitter and receiver are possible and include both side-by-side arrangements and the use of a single transducer to both transmit and receive a reflected signal. In other embodiments, any number, configuration, and type of sensor(s) may be used.

The electronic detection device 118 comprises electronic circuitry, connected to the receiver portion 116B of the sensor 116, for receiving the signal transmitted from the electronic transmitting device 114, through the transmitter portion 116A of the sensor 116, through the fluid delivery line 104, to the receiver portion 116B of the sensor 116, to the electronic detection device 118. The electronic detection device 118 comprises an analog-to-digital converter which is electronically connected to the sensor 116 for converting the signal received by the receiver portion 116B of the sensor from analog to digital and communicating the digital reading to the processing device 108. The processing device 108 then determines, based on the digital reading, whether air, fluid, or some combination thereof is disposed in the fluid delivery line 104 at the sensor 116 by executing the programming code containing the one or more algorithms.

The programming code implemented by the processing device 108 is configured to operate the sensor 116 at a modified frequency which is different than a resonant frequency of the sensor 116 in order to reduce the amplitude of an output of the signal transmitted from the transmitter portion 116A of the sensor 116 to a level which is lower than a saturation level of the electronic detection device 118 comprising the analog-to-digital converter. The resonant frequency of the sensor 116 is the frequency at which the output of the signal transmitted from the transmitter portion 116A of the sensor 116 is maximized for a given transfer medium (such as the fluid delivery line 104 filled with infusion fluid).

By reducing the amplitude of the output of the signal transmitted from the transmitter portion 116A of the sensor 116 to a level which is lower than the saturation level of the electronic detection device 118 comprising the analog-to-digital converter, the reliability and accuracy of the processing device 108 detecting air, fluid, or some combination thereof in the fluid delivery line 104 is increased. This is because when the amplitude of an output of a signal transmitted from a sensor to an analog-to-digital converter is greater than a saturation level of the analog-to-digital converter, the accuracy and reliability of the analog-to-digital converter is reduced which may lead to errors in detecting air, fluid, or some combination thereof in the fluid delivery line. The resonant frequency of the sensor 116, the saturation level of the electronic detection device 118, and the amplitude of the output of the signal transmitted from the transmitter portion 116A of the sensor 116, set to be lower than the saturation level of the electronic detection device 118, each may be determined and/or set during calibration of the sensor 116 and the electronic detection device 118, or advantageously may be set at other times such as during use in the field.

Figure 2:
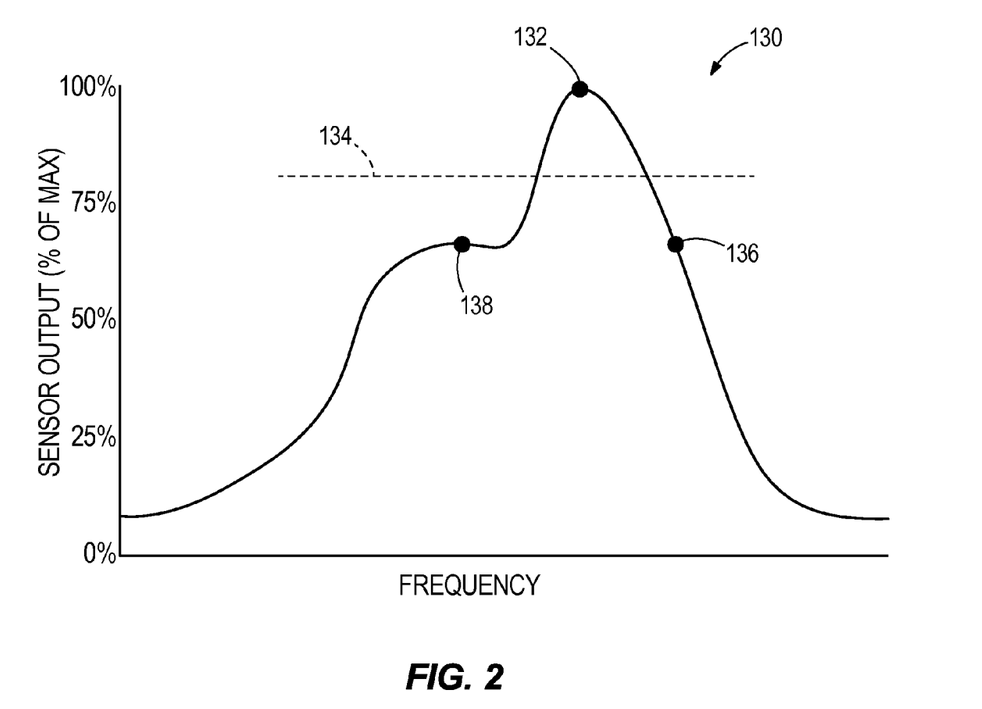
FIG. 2 is a graph illustrating in one embodiment of the disclosure how shifting the frequency of a sensor of the infusion system of FIG. 1 to a modified frequency which is different than the resonant frequency of the sensor may avoid over-saturating an electronic detection device of FIG. 1.

FIG. 2 is a graph 130 illustrating in one embodiment of the disclosure how shifting the frequency of the sensor 116 of FIG. 1 to a modified frequency which is different than the resonant frequency of the sensor 116 may avoid over-saturating the electronic detection device 118 of FIG. 1. Frequency of the sensor 116 of FIG. 1 is plotted on the X-axis of the graph 130. Output of the sensor 116 of FIG. 1 expressed as a percentage of the maximum sensor output is plotted on the Y-axis of the graph 130. The resonant frequency 132 is the frequency at which the output of the sensor 116 of FIG. 1 is maximized. The electronic detection device 118 of FIG. 1 is over-saturated when the output of the sensor 116 of FIG. 1 is above the saturation level 134. By reducing the output of the sensor 116 of FIG. 1 to a percentage of maximum which is lower than the saturation level 134, over-saturation of the electronic detection device 118 of FIG. 1 is avoided. As shown, this may be done by changing the frequency of the sensor 116 of FIG. 1 to a modified frequency which is different than the resonant frequency 132 to reduce the output of the sensor 116 of FIG. 1 to a level which is lower than the saturation level 134 of the electronic detection device 118 of FIG. 1. For instance, at point 136 the frequency of the sensor 116 of FIG. 1 has been increased beyond the resonant frequency 132 to reduce the output of the sensor 116 of FIG. 1 to a level which is lower than the saturation level 134 of the electronic detection device 118 of FIG. 1 to avoid over-saturating the electronic detection device 118. Similarly, at point 138 the frequency of the sensor 116 of FIG. 1 has been decreased below the resonant frequency 132 to reduce the output of the sensor 116 of FIG. 1 to a level which is lower than the saturation level 134 of the electronic detection device 118 of FIG. 1 to avoid over-saturating the electronic detection device 118.

Figure 3:
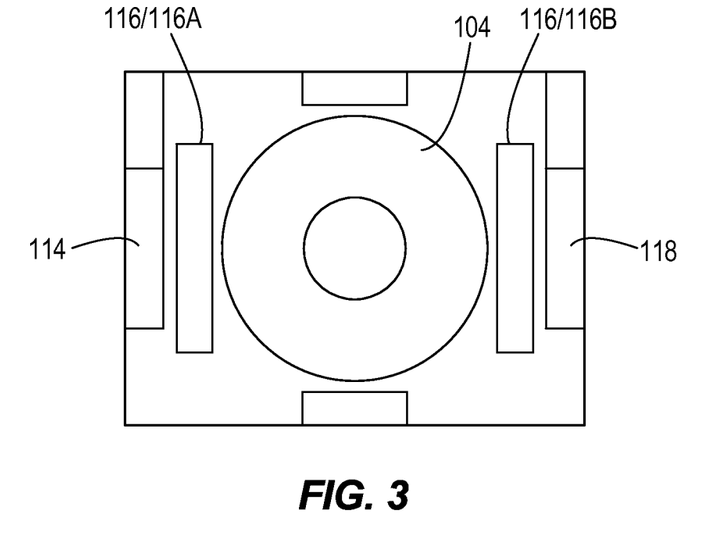
FIG. 3 illustrates a cross-section through one embodiment of a segment of fluid delivery line coupled to an electronic transmitting device, a transmitter portion of a sensor, a receiver portion of the sensor, and an electronic detection device.

FIG. 3 illustrates a cross-section through one embodiment of a segment of fluid delivery line 104 coupled to the electronic transmitting device 114, the transmitter portion 116A of the sensor 116, the receiver portion 116B of the sensor 116, and the electronic detection device 118. The transmitter and receiver portions 116A and 116B of the sensor 116 comprises piezoelectric crystals compressed against each side of the fluid delivery line 104 creating more surface area for uniform acoustic coupling and better signal to noise ratio. This arrangement of the transmitter and receiver portions 116A and 116B of the sensor 116 enables the transmission and detection of an ultrasonic signal through a target volume of the fluid delivery line 104. The electronic transmitting device 114 generates a nominal 5.25 MHz ultrasonic signal directed from the transmitter 116A portion of the sensor 116, through the fluid delivery line 104, to the receiver portion 116B of the sensor 116 connected to the electronic detection device 118. When fluid is present in the fluid delivery line 104 at the position of the sensor 116, the receiver portion 116B of the sensor 116 and the electronic detection device 118 generate a larger electrical signal than when air is present at the same position. Because of an inversion in the electronics of the electronic detection device 118, the software of the processing device 108 will receive a low signal when fluid is present at the location of the sensor 116, and a high signal when air is present at the location of the sensor 116. When a cassette is loaded into the pump device 106, the segment of the fluid delivery line 104 distal to the cassette is clamped into place in front of the sensor 116. This enables reliable and repeatable sensor performance over multiple cassettes.

Figure 4:
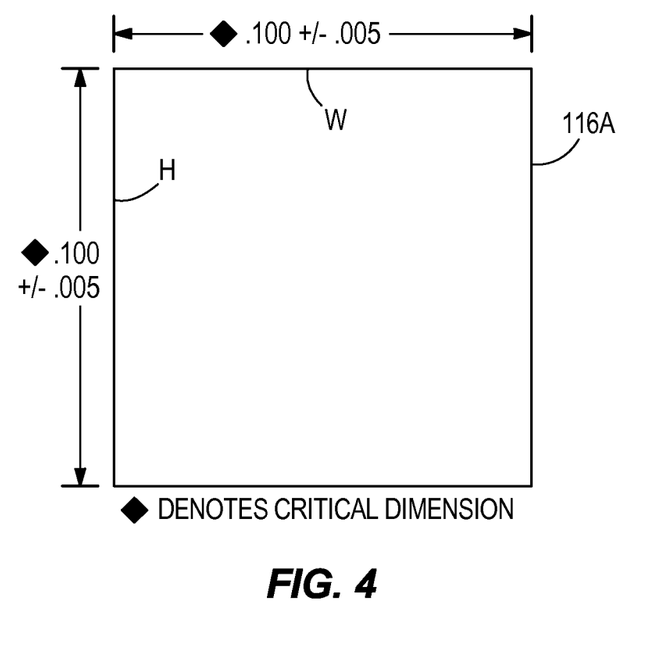
FIG. 4 illustrates a top view through one embodiment of the piezoelectric crystals of the transmitter portion of the sensor of FIG. 3.

FIG. 4 illustrates a top view through one embodiment of the piezoelectric crystals of the transmitter portion 116A of the sensor 116 of FIG. 3. As shown, the height H of the transmitter portion 116A comprises 0.100 inches and the width W of the transmitter portion 116A comprises 0.100 inches. The dimensions of the receiver portion 116B of the sensor 116 of FIG. 1 are identical to the transmitter portion 116A. In other embodiments, the dimensions of the transmitter and receiver portions 116A and 116B of the sensor 116 may vary.

The ability of the ultrasonic signal to propagate from the transmitter portion 116A to the receiver portion 116B of the sensor 116 is governed by the acoustic impedance of the materials. The matching layers of the transducers of the transmitter and receiver portions 116A and 116B are designed to control the amplitude of the reflections at the piezo-matching layer and matching layer-fluid delivery line interfaces. The other significant component of the signal path is the fluid or air inside the fluid delivery line 104. The acoustic impedances (Za) @ 20° C. of interest are as follows: water=$1.5 \times 10^6$ kg/(m² s); PVC=$3.3 \times 10^6$ kg/(m² s); and air=413.2 kg/(m² s). Reflections of the ultrasonic signal occur at material boundaries and are governed by the differences in acoustic impedance. The reflection coefficient (RC) is defined as: RC=(Za−Za1)/(Za+Za1). A high RC indicates that the signal will not pass through the boundary. For the PVC to water interface, the RC=0.375 which indicates that a majority of the signal will pass through the interface. For the PVC to air interface, the RC=0.999 which indicates that a negligible, but non-zero portion of the signal energy will pass through the interface.

The electronic detection device 118 converts the signal received by the receiver portion 116B of the sensor 116 from an analog signal to a digital electrical signal as governed by the equation: Vout=$\lambda$ Tpiezo $\sigma$/Drvr, where Vout=the electrical signal received by the receiver portion 116B of the sensor; $\lambda$=the strain on the piezo crystal due to the ultrasonic wave; $\sigma$=the stress on the piezo crystal due to the ultrasonic wave; Tpiezo=the thickness of the piezo crystal; Drvr=the mechanical displacement of the piezo by the ultrasonic crystal. Thus, when fluid is in the fluid delivery line 104, the receiver portion 116B of the sensor 116 is able to collect a large amount of ultrasonic energy since fluid is a better conductor than air. This appears as a low voltage at the analog-to-digital converter of the electronic detection device 118 because the signal received by the receiver portion 116B of the sensor 116 is inverted electrically. The position of the fluid (for instance a fluid droplet) inside the fluid delivery line 104 relative to the transmitter and receiver portions 116A and 116B of the sensor 116 also influences the amount of energy the receiver portion 116B of the sensor detects. When air is in the fluid delivery line 104, the receiver portion 116B of the sensor 116 collects little energy.

The processing device 108 of FIG. 1 includes software components that receive the signal received by the receiver portion 116B of the sensor 116 and converted to a digital signal though the electronic detection device 118. The processing device 108 processes the received digital signal, and generates an alarm, using the alarm device 110 of FIG. 1, when the one or more algorithms stored in the programming code indicates that an amount of air over the air threshold is present.

Figure 5:
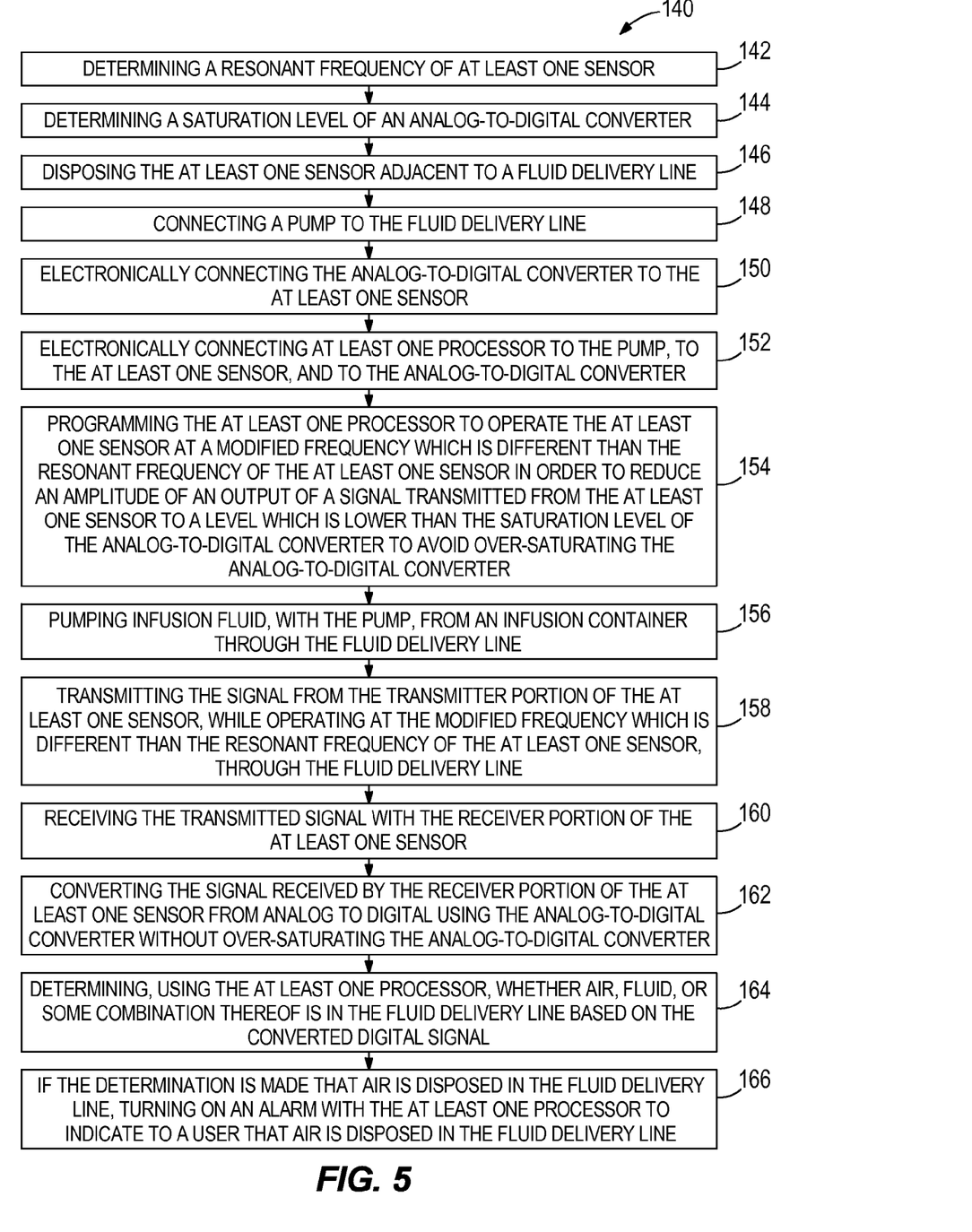
FIG. 5 illustrates a flowchart of one embodiment of a method for arranging and using an infusion system.

FIG. 5 illustrates a flowchart of one embodiment of a method 140 for arranging and using an infusion system. The method 140 may utilize the infusion system of FIG. 1. In other embodiments, the method 140 may utilize varying systems. In step 142, a resonant frequency of at least one sensor is determined. Step 142 may be done during calibration of the at least one sensor. In another embodiment, step 142 may be done at a varying time such as when in use in the field. In step 144, a saturation level of an analog-to-digital converter is determined. Step 144 may be done during calibration of the analog-to-digital converter. Advantageously in another embodiment, step 144 may be done at a varying time such as when in use in the field. In step 146, the at least one sensor is disposed adjacent to a fluid delivery line. In one embodiment, step 146 may comprise disposing a transmitter portion of the at least one sensor and a receiver portion of the at least one sensor on opposed sides of the fluid delivery line. In step 148, a pump is connected to the fluid delivery line. In step 150, the analog-to-digital converter is electronically connected to the at least one sensor. In step 152, at least one processor is electronically connected to the pump, to the at least one sensor, and to the analog-to-digital converter.

In step 154, the at least one processor is programmed to operate the at least one sensor at a modified frequency which is different than the resonant frequency of the at least one sensor in order to reduce an amplitude of an output of a signal transmitted from the at least one sensor to a level which is lower than the saturation level of the analog-to-digital converter to avoid over-saturating the analog-to-digital converter. In one embodiment, step 154 may be done during calibration of the at least one sensor. Advantageously in another embodiment, step 154 may be done at a varying time such as when in use in the field. In still another embodiment, any or each of steps 142, 144, and 154 may be done prior to steps 146, 148, 150, and 152.

In step 156, infusion fluid is pumped, with the pump, from an infusion container through the fluid delivery line. In step 158, the signal is transmitted from the transmitter portion of the at least one sensor, while operating at the modified frequency which is different than the resonant frequency of the at least one sensor, through the fluid delivery line. In step 160, the transmitted signal is received with the receiver portion of the at least one sensor. In step 162, the signal received by the receiver portion of the at least one sensor is converted from analog to digital using the analog-to-digital converter without over-saturating the analog-to-digital converter. In step 164, a determination is made, using the at least one processor, whether air, fluid, or some combination thereof is in the fluid delivery line based on the converted digital signal. In step 166, if the determination is made in step 164 that air is disposed in the fluid delivery line, the at least one processor turns on an alarm to indicate to a user that air is disposed in the fluid delivery line. In one embodiment, if the determination is made in step 164 that air is disposed in the fluid delivery line, then in step 166 the at least one processor turns on the alarm and shuts down the infusion system to stop the delivery of infusion fluid through the fluid delivery line. In other embodiments, the method 140 may be altered to vary the order or substance of any of the steps, to delete one or more steps, or to add one or more steps.

Figure 6:
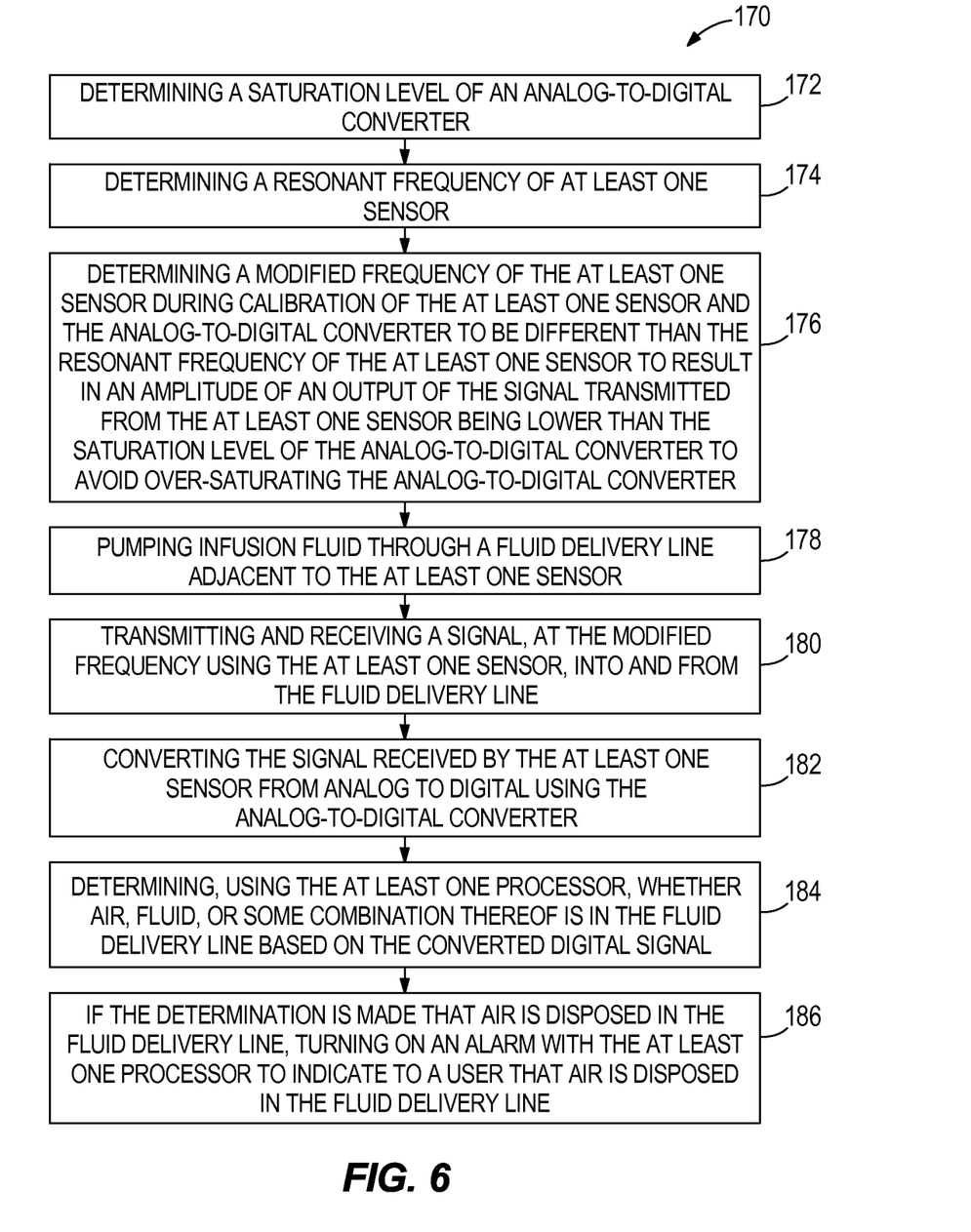
FIG. 6 illustrates a flowchart of one embodiment of a method for detecting air in a fluid delivery line of an infusion system.

FIG. 6 illustrates a flowchart of one embodiment of a method 170 for detecting air in a fluid delivery line of an infusion system. The method 170 may utilize the infusion system of FIG. 1. In other embodiments, the method 170 may utilize varying systems. In step 172, a saturation level of an analog-to-digital converter may be determined. Step 172 may be done during calibration of the analog-to-digital converter. In other embodiments, step 172 may be done at a varying time such as when in use in the field. In step 174, a resonant frequency of at least one sensor is determined. Step 174 may be done during calibration of the at least one sensor. Advantageously in other embodiments, step 174 may be done at a varying time such as when in use in the field. In step 176, a modified frequency of the at least one sensor may be determined during calibration of the at least one sensor and the analog-to-digital converter to be different than the resonant frequency of the at least one sensor to result in an amplitude of an output of the signal transmitted from the at least one sensor being lower than the saturation level of the analog-to-digital converter to avoid over-saturating the analog-to-digital converter. In other embodiments, step 176 may be done at a varying time such as when in use in the field.

In step 178, infusion fluid is pumped through a fluid delivery line adjacent to the at least one sensor. In step 180, a signal is transmitted and received, using the at least one sensor, into and from the fluid delivery line. Step 180 further comprises the at least one sensor operating, using at least one processor, at the modified frequency which is different than the resonant frequency of the at least one sensor in order to reduce an amplitude of an output of the signal transmitted from the at least one sensor to a level which is lower than the saturation level of the analog-to-digital converter to avoid over-saturating the analog-to-digital converter. In one embodiment, step 180 comprises transmitting the signal from a transmitter portion of the at least one sensor disposed on one side of the fluid delivery line, while operating at the modified frequency which is different than the resonant frequency of the at least one sensor, to a receiver portion of the at least one sensor disposed on an opposed side of the fluid delivery line.

In step 182, the signal received by the at least one sensor is converted from analog to digital using the analog-to-digital converter. In step 184, a determination is made using the at least one processor whether air, fluid, or some combination thereof is in the fluid delivery line based on the converted digital signal. In step 186, if the determination is made in step 184 that air is disposed in the fluid delivery line, the at least one processor turns on an alarm to indicate to a user that air is disposed in the fluid delivery line. In one embodiment, if the determination is made in step 184 that air is disposed in the fluid delivery line, then in step 186 the at least one processor turns on the alarm and shuts down the infusion system to stop the delivery of infusion fluid through the fluid delivery line. In other embodiments, the method 170 may be altered to vary the order or substance of any of the steps, to delete one or more steps, or to add one or more steps.

Figure 7:
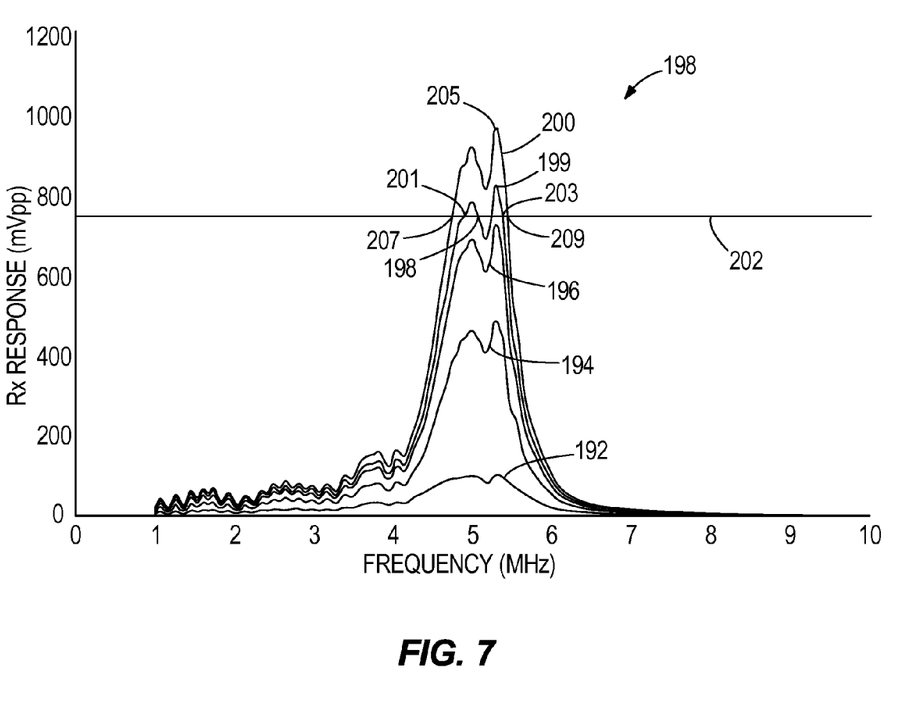
FIG. 7 is a graph illustrating five different curves showing for five different illustrative sensors, which could each be tried as the sensor in the infusion system of FIG. 1, how their respective signal strength varies as their modified frequency varies.

FIG. 7 is a graph 190 illustrating five different curves 192, 194, 196, 198, and 200 showing for five different illustrative sensors, which could each be tried for the sensor 116 in the infusion system of FIG. 1, how their respective signal strength varies as their modified frequency varies. The frequency performance for each sensor is plotted on the X-axis of the graph 190. The signal output of each sensor is plotted on the Y-axis of the graph 190. The electronic detection device 118 of FIG. 1 requires a minimum useful signal strength of greater than or equal to 100 mVpp. The electronic detection device 118 of FIG. 1 is over-saturated when the output of any of the sensors exceeds the saturation level 202 which is approximately 750 mVpp.

Curve 192 has a sensor output of below the minimum useful signal of 100 mVpp no matter how the modified frequency is varied. As a result this sensor should not be used because the signal is too weak. Curve 194 has a sensor output of below the minimum useful signal of 100 mVpp at some modified frequencies, and a sensor output of greater than or equal to the minimum useful signal of 100 mVpp at other modified frequencies yet the entire curve is below the saturation level 202 of 750 mVpp. As a result, this sensor can be used at any modified frequency which results in a signal output of greater than or equal to the minimum useful signal of 100 mVpp which is in the approximate range of between 4.3 MHz to 5.7 MHz as shown by curve 194. Curve 196 has a sensor output of below the minimum useful signal of 100 mVpp at some modified frequencies, and a sensor output of greater than or equal to the minimum useful signal of 100 mVpp at other modified frequencies yet the entire curve is below the saturation level 202 of 750 mVpp. As a result, this sensor can be used at any modified frequency which results in a signal output of greater than or equal to the minimum useful signal of 100 mVpp which is in the approximate range of between 4.2 MHz to 5.8 MHz as shown by curve 196.

Curve 198 has a sensor output of below the minimum useful signal of 100 mVpp at some modified frequencies, and a sensor output of greater than or equal to the minimum useful signal of 100 mVpp at other modified frequencies. Additionally, curve 198 has a sensor output of below the saturation level 202 of 750 mVpp at some modified frequencies, and a sensor output of above the saturation level 202 of 750 mVpp at other modified frequencies. As a result, this sensor can be used at any modified frequency which results in a signal output of greater than or equal to the minimum useful signal of 100 mVpp and results in a signal output of less than the saturation level 202 of 750 mVpp which is in the approximate range of between 3.4 MHz to 5.9 MHz as shown by curve 198. In order to obtain a modified frequency which results in a signal output of greater than or equal to the minimum useful signal of 100 mVpp and results in a signal output of less than the saturation level 202 of 750 mVpp, Applicants have discovered that the modified frequency for curve 198 needs to be within ±36% from the resonant frequency 199 of 5.3 MHz and within ±31% from the minimum or maximum saturation frequencies 201 and 203 which result in the saturation level of 750 mVpp. Preferably, the highest modified frequency is selected which results in a signal output as high as possible without exceeding the saturation level and is above the minimum useful signal strength.

Curve 200 has a sensor output of below the minimum useful signal of 100 mVpp at some modified frequencies, and a sensor output of greater than or equal to the minimum useful signal of 100 mVpp at other modified frequencies. Additionally, curve 200 has a sensor output of below the saturation level 202 of 750 mVpp at some modified frequencies, and a sensor output of above the saturation level 202 of 750 mVpp at other modified frequencies. As a result, this sensor can be used at any modified frequency which results in a signal output of greater than or equal to the minimum useful signal strength of 100 mVpp and results in a signal output of less than the saturation level 202 of 750 mVpp which is in the approximate range of between 3.5 MHz to 6.0 MHz as shown by curve 200. In order to obtain a modified frequency which results in a signal output of greater than or equal to the minimum useful signal of 100 mVpp and results in a signal output of less than the saturation level 202 of 750 mVpp, Applicants have discovered that the modified frequency for curve 200 needs to be within ±34% from the resonant frequency 205 of 5.3 MHz and within ±27% from the minimum or maximum saturation frequencies 207 and 209 which result in the saturation level of 750 mVpp. Preferably, the highest modified frequency is selected which results in a signal output as high as possible without exceeding the saturation level and which is above the minimum useful signal strength. In one embodiment, this modified frequency may be chosen so that the signal output is within 5% of the saturation level. In another embodiment, this modified frequency may be chosen so that the signal output is within 10% of the saturation level. In other embodiments, varied modified frequencies may be chosen.

In other embodiments, other sensors may be used which have different sensor signal strength performance at varied modified frequencies. In one embodiment, a sensor may be used which has a modified frequency of within ±50% from the resonant frequency and within ±50% from a saturation frequency. In another embodiment, a sensor may be used which has a modified frequency of within ±40% from the resonant frequency and within ±40% from a saturation frequency. In another embodiment, a sensor may be used which has a modified frequency of within ±30% from the resonant frequency and within ±30% from a saturation frequency. In another embodiment, a sensor may be used which has a modified frequency of within ±20% from the resonant frequency and within ±20% from a saturation frequency. In another embodiment, a sensor may be used which has a modified frequency of within ±10% from the resonant frequency and within ±10% from a saturation frequency.

Figure 8:
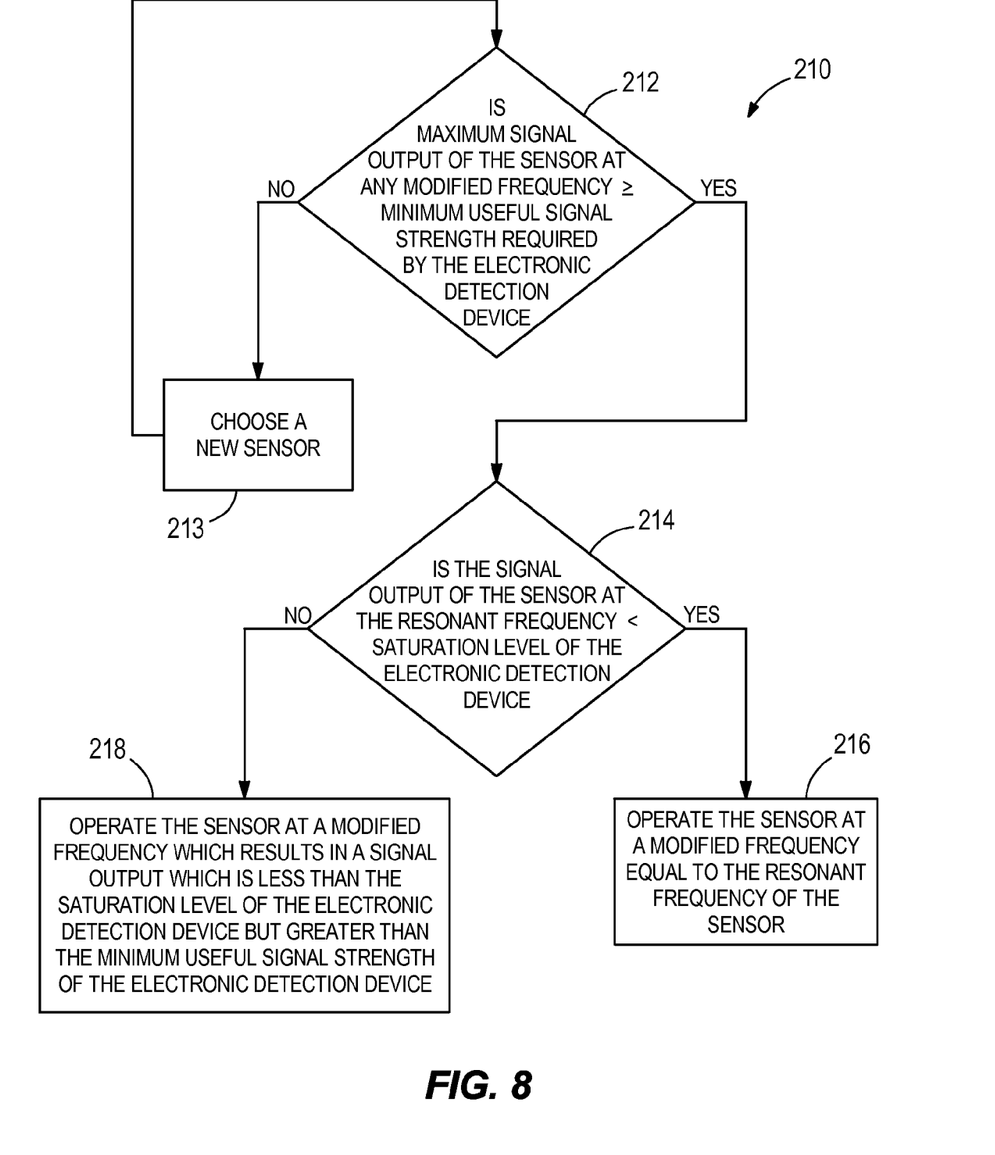
FIG. 8 illustrates a flowchart of one embodiment of a method for determining the modified frequency of an infusion system.

FIG. 8 illustrates a flowchart of one embodiment of a method 210 for determining the modified frequency of an infusion system. The method 210 may utilize the infusion system of FIG. 1. In other embodiments, the method 210 may utilize varying systems. The method 210 may be incorporated into any of the other methods disclosed herein including the methods illustrated in FIGS. 5 and 6 of this disclosure. In step 212, a determination is made as to whether the maximum signal output of the sensor at any modified frequency is greater than or equal to the minimum useful signal strength required by the electronic detection device. If the determination is made in step 212 that the maximum signal output of the sensor at any modified frequency is not greater than or equal to the minimum useful signal strength then in step 213 a new sensor is chosen and then step 212 is repeated until the determination is made in step 212 that the maximum signal output of the sensor at any modified frequency is greater than or equal to the minimum useful signal strength. Once the determination is made in step 212 that the maximum signal output of the sensor at any modified frequency is greater than or equal to the minimum useful signal strength, then the method proceeds from step 212 to step 214.

In step 214, a determination is made as to whether the signal output of the sensor at the resonant frequency is less than the saturation level of the electronic detection device. If the determination is made in step 214 that the signal output of the sensor at the resonant frequency is less than the saturation level of the electronic detection device, then the method proceeds to step 216. In step 216, the sensor is operated at a modified frequency which is equal to the resonant frequency of the sensor.

If the determination is made in step 214 that the signal output of the sensor at the resonant frequency is not less than the saturation level of the electronic detection device, then the method proceeds to step 218. In step 218, the sensor is operated at a modified frequency which results in a signal output which is less than the saturation level of the electronic detection device but greater than the minimum useful signal strength of the electronic detection device. Preferably, in step 218 the sensor is operated at the highest modified frequency which results in a signal output as high as possible without exceeding the saturation level of the electronic detection device and which is above the minimum useful signal strength of the electronic detection device. In one embodiment of step 218, the sensor may be operated at a modified frequency within 5% of the saturation level. In another embodiment of step 218, the sensor may be operated at a modified frequency within 10% of the saturation level. In other embodiments of step 218, the sensor may be operated at varied modified frequencies. In other embodiments, the method 210 may be altered to vary the order or substance of any of the steps, to delete one or more steps, or to add one or more steps.

One or more embodiments of the disclosure may improve the accuracy and reliability of the detection of air in infusion systems. One or more embodiments of the disclosure may be incorporated during calibration of one or more components of the infusion system. One or more embodiments of the disclosure may be done in the field without having to replace existing sensors of the infusion system by performing a field service procedure. This reduces the cost of sensor replacement and reduces the amount of replacement parts that must be kept in inventory. The disclosure also can accommodate greater variability and thus increases the yield of sensor assemblies that can be used.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

The invention claimed is:

1. An infusion system for being operatively connected to a fluid delivery line and to an infusion container containing an infusion fluid, the infusion system comprising:
   a pump;
   at least one sensor disposed adjacent to the fluid delivery line and configured to transmit and receive a first signal to detect whether there is air in the fluid delivery line, the at least one sensor configured to transmit a second signal, the second signal indicative of whether there is air in the fluid delivery line;
   an electronic detection device electronically connected to the at least one sensor and configured to receive the second signal;
   at least one processor in electronic communication with the pump, the at least one sensor, and the electronic detection device; and
   a memory in electronic communication with the at least one processor, wherein the memory comprises programming code for execution by the at least one processor, and the programming code is configured to operate the at least one sensor at a resonant frequency or at a modified frequency which is different than the resonant frequency;
   wherein the programming code is configured to determine whether the electronic detection device would be saturated as a result of operating the at least one sensor at the resonant frequency;

wherein the programming code is configured such that if the programming code determines that operating the at least one sensor at the resonant frequency would saturate the electronic detection device, the programming code operates the at least one sensor at the modified frequency, wherein operating the at least one sensor at the modified frequency causes the amplitude of the second signal to be lower than required to saturate the electronic detection device and greater than the minimum level of useful signal strength of the electronic detection device; and wherein the programming code is configured such that if the programming code determines that operating the at least one sensor at the resonant frequency causes the amplitude of the second signal to be lower than the saturation level of the electronic detection device and greater than the minimum useful signal strength of the electronic detection device, the programming code operates the at least one sensor at the resonant frequency.

2. The apparatus of claim 1 wherein the modified frequency is within .+−0.50% of the resonant frequency and within .+−0.50% of a saturation frequency which causes the analog-to-digital converter to saturate.

3. The infusion system of claim 1, wherein the electronic detection device comprises an analog to digital converter, the analog to digital converter configured to convert the second signal from analog to digital.

4. A method for detecting air in a fluid delivery line of an infusion system comprising:
pumping infusion fluid through a fluid delivery line adjacent to at least one sensor;
transmitting and receiving a first signal using the at least one sensor into and from the fluid delivery line;
transmitting a second signal from the at least one sensor to an electronic detection device, the second signal indicative of whether there is air in the fluid delivery line;
operating, using at least one processor, the at least one sensor at a resonant frequency or at a modified frequency which is different than the resonant frequency;
determining whether the electronic detection device would be saturated as a result of operating the at least one sensor at the resonant frequency;
wherein if it is determined that operating the at least one sensor at the resonant frequency would saturate the electronic detection device, operating the at least one sensor at the modified frequency, wherein operating the at least one sensor at the modified frequency causes the amplitude of the second signal to be lower than required to saturate the electronic detection device and greater than the minimum level of useful signal strength of the electronic detection device; and
wherein if it is determined that operating the at least one sensor at the resonant frequency causes the amplitude of the second signal to be lower than the saturation level of the electronic detection device and greater than the minimum useful signal strength of the electronic detection device, operating the at least one sensor at the resonant frequency.

5. The method of claim 4 further comprising determining, using the at least one processor, whether air is in the fluid delivery line based on the second signal.

6. The method of claim 4 further comprising determining the resonant frequency of the at least one sensor.

7. The method of claim 6 further comprising calibrating the at least one sensor to determine the resonant frequency of the at least one sensor.

8. The method of claim 7 further comprising determining the modified frequency which is different than the resonant frequency of the at least one sensor during calibration of the at least one sensor.

9. The method of claim 4 further comprising determining the saturation level of the electronic detection device.

10. The method of claim 4 further comprising selecting the modified frequency to be within .+−0.50% of the resonant frequency and within .+−0.50% of a saturation frequency which causes the analog-to-digital converter to saturate.

11. The method of claim 4, wherein the electronic detection device comprises an analog to digital converter, the analog to digital converter configured to convert the second signal from analog to digital.

12. A method for arranging and using an infusion system comprising:
determining a resonant frequency of at least one sensor;
determining a saturation level of an electronic detection device;
disposing the at least one sensor adjacent to a fluid delivery line;
connecting a pump to the fluid delivery line;
electronically connecting the electronic detection device to the at least one sensor;
electronically connecting at least one processor to the pump, to the at least one sensor, and to the electronic detection device; and
programming the at least one processor to operate the at least one sensor at a resonant frequency or at a modified frequency which is different than the resonant frequency;
determining whether the electronic detection device would be saturated as a result of operating the at least one sensor at the resonant frequency;
wherein if it is determined that operating the at least one sensor at the resonant frequency would saturate the electronic detection device, operating the at least one sensor at the modified frequency, wherein operating the at least one sensor at the modified frequency causes the amplitude of a signal from the at least one sensor to be lower than required to saturate the electronic detection device and greater than the minimum level of useful signal strength of the electronic detection device; and
wherein if it is determined that operating the at least one sensor at the resonant frequency causes the amplitude of the signal from the at least one sensor to be lower than the saturation level of the electronic detection device and greater than the minimum useful signal strength of the electronic detection device, operating the at least one sensor at the resonant frequency.

13. The method of claim 12 wherein the determining the resonant frequency of the at least one sensor is done during calibration of the at least one sensor.

14. The method of claim 12 wherein the determining the saturation level of the electronic detection device is done during calibration of the electronic detection device.

15. The method of claim 12 wherein the programming the at least one processor is done during calibration of the at least one processor.

16. The method of claim 12 wherein the determining the resonant frequency of the at least one sensor, the determining the saturation level of the electronic detection device, and the programming the at least one processor are all done prior to the disposing and the connecting.

17. The method of claim 12 wherein the disposing the at least one sensor adjacent to the fluid delivery line comprises disposing a transmitter portion of the at least one sensor and a receiver portion of the at least one sensor on opposed sides of the fluid delivery line.

18. The method of claim 12 further comprising converting an output signal transmitted from the sensor to the electronic detection device from analog to digital using an analog-to-digital converter without over-saturating the analog-to-digital converter.

19. The method of claim 18 further comprising determining, using the at least one processor, whether air is in the fluid delivery line based on the output signal.

20. The method of claim 12, wherein the electronic detection device comprises an analog to digital converter.

* * * * *

UNITED STATES PATENT AND TRADEMARK OFFICE
CERTIFICATE OF CORRECTION

PATENT NO. : 9,707,341 B2
APPLICATION NO. : 14/289796
DATED : July 18, 2017
INVENTOR(S) : John Hicks Dumas, III It is certified that error appears in the above-identified patent and that said Letters Patent is hereby corrected as shown below:

In the Claims

In Column 13 at Line 23, In Claim 2, change ".+-0.50%" to --±50%--.

In Column 13 at Line 24, In Claim 2, change ".+-0.50%" to --±50%--.

In Column 14 at Line 12 (approx.), In Claim 10, change ".+-0.50%" to --±50%--.

In Column 14 at Line 13 (approx.), In Claim 10, change ".+-0.50%" to --±50%--.

Signed and Sealed this
Second Day of January, 2018

Joseph Matal
*Performing the Functions and Duties of the*
*Under Secretary of Commerce for Intellectual Property and*
*Director of the United States Patent and Trademark Office*